(12) United States Patent
Bobey et al.

(10) Patent No.: US 10,518,048 B2
(45) Date of Patent: Dec. 31, 2019

(54) COORDINATED CONTROL OF HFCWO AND COUGH ASSIST DEVICES

(71) Applicant: Hill-Rom Services PTE Limited, Singapore (SG)

(72) Inventors: John A. Bobey, Daniel Island, SC (US); Jason A. Penninger, Indianapolis, IN (US); Brian E. Byrd, Summerville, SC (US); Brian C. Becker, Bloomington, MN (US); Michael A. Roux, Eagan, MN (US); Kristin McFall

(73) Assignee: Hill-Rom Services, PTE Ltd., Singapore (SG)

( * ) Notice: Subject to any disclaimer, the term of this patent is extended or adjusted under 35 U.S.C. 154(b) by 736 days.

(21) Appl. No.: 15/206,760

(22) Filed: Jul. 11, 2016

(65) Prior Publication Data
US 2017/0027813 A1 Feb. 2, 2017

Related U.S. Application Data

(60) Provisional application No. 62/199,714, filed on Jul. 31, 2015.

(51) Int. Cl.
*A61M 16/00* (2006.01)
(52) U.S. Cl.
CPC .... *A61M 16/0006* (2014.02); *A61M 16/0009* (2014.02); *A61H 2205/084* (2013.01); *A61M 16/0066* (2013.01); *A61M 2205/505* (2013.01)
(58) Field of Classification Search
CPC .............................. A61M 16/00; A61M 16/202
See application file for complete search history.

(56) References Cited

U.S. PATENT DOCUMENTS

| | | | |
|---|---|---|---|
| 1,833,103 A | 11/1931 | Anderson | |
| 2,523,844 A | 12/1950 | Emerson | |
| 2,699,163 A | 1/1955 | Engstrom | |
| 2,762,366 A | 9/1956 | Huxley, III et al. | |
| 2,772,673 A | 12/1956 | Huxley, III | |
| 2,779,329 A | 1/1957 | Huxley, III et al. | |
| 2,780,222 A | 2/1957 | Polzin et al. | |

(Continued)

FOREIGN PATENT DOCUMENTS

| | | |
|---|---|---|
| DE | 44 33 068 A1 | 3/1996 |
| DE | 197 26 281 A1 | 1/1998 |

(Continued)

OTHER PUBLICATIONS

Dima Italia SRL. Mini Pegaso Cough brochure (2 pages).

(Continued)

*Primary Examiner* — Tan-Uyen T Ho
*Assistant Examiner* — Cana A Gallegos
(74) *Attorney, Agent, or Firm* — Barnes & Thornburg LLP

(57) ABSTRACT

A respiratory therapy apparatus includes components operable to simultaneously provide a High Frequency Chest Wall Oscillation (HFCWO) therapy and a Mechanical Insufflation/Exsufflation (MIE) therapy to a patient. The respiratory therapy apparatus includes a controller that controls a synchronization of the HFCWO therapy and the MIE therapy to provide respiratory therapy to the patient to effectively clear mucous or induce deep sputum from the lungs of patient.

22 Claims, 3 Drawing Sheets

(56) References Cited

U.S. PATENT DOCUMENTS

| | | | |
|---|---|---|---|
| 2,832,335 A | 4/1958 | Huxley, III et al. |
| 2,845,062 A | 7/1958 | Kling et al. |
| 2,918,917 A | 12/1959 | Emerson |
| 3,120,228 A | 2/1964 | Huxley, III |
| 3,333,581 A | 8/1967 | Robinson et al. |
| 3,548,811 A | 12/1970 | Wilson |
| 3,566,862 A | 3/1971 | Schuh |
| 3,896,794 A | 7/1975 | McGrath |
| 4,003,373 A | 1/1977 | Spelio |
| 4,054,134 A | 10/1977 | Kritzer |
| 4,062,358 A | 12/1977 | Kritzer |
| 4,079,733 A | 3/1978 | Denton et al. |
| 4,226,233 A | 10/1980 | Kritzer |
| 4,398,531 A | 8/1983 | Havstad |
| 4,424,806 A | 1/1984 | Newman et al. |
| 4,637,386 A | 1/1987 | Baum |
| 4,719,910 A | 1/1988 | Jensen |
| 4,805,612 A | 2/1989 | Jensen |
| 4,821,709 A | 4/1989 | Jensen |
| 4,838,263 A | 6/1989 | Warwick et al. |
| 4,971,042 A | 11/1990 | Lerman |
| 4,977,889 A | 12/1990 | Budd |
| 5,056,505 A | 10/1991 | Warwick et al. |
| 5,137,432 A | 8/1992 | Tsai |
| 5,163,818 A | 11/1992 | Betsill et al. |
| 5,360,323 A | 11/1994 | Hsieh |
| 5,398,676 A | 3/1995 | Press et al. |
| 5,453,081 A | 9/1995 | Hansen |
| 5,508,908 A | 4/1996 | Kazama et al. |
| 5,529,467 A | 6/1996 | Rometsch |
| 5,551,843 A | 9/1996 | Hauser |
| 5,682,878 A | 11/1997 | Ogden |
| 5,704,346 A | 1/1998 | Inoue |
| 5,769,797 A | 6/1998 | Van Brunt et al. |
| 5,830,164 A | 11/1998 | Cone et al. |
| 5,848,878 A | 12/1998 | Conti et al. |
| 5,997,488 A | 12/1999 | Gelfand et al. |
| 6,030,353 A | 2/2000 | Van Brunt |
| 6,036,662 A | 3/2000 | Van Brunt et al. |
| 6,066,101 A | 5/2000 | Johnson et al. |
| 6,102,042 A | 8/2000 | Hete et al. |
| 6,176,235 B1 | 1/2001 | Benarrouch et al. |
| 6,179,793 B1 | 1/2001 | Rothman et al. |
| 6,209,540 B1 | 4/2001 | Sugiura et al. |
| 6,210,345 B1 | 4/2001 | Van Brunt |
| 6,254,556 B1 | 7/2001 | Hansen et al. |
| 6,290,660 B1 | 9/2001 | Epps et al. |
| 6,332,463 B1 | 12/2001 | Farrugia et al. |
| 6,340,025 B1 | 1/2002 | Van Brunt |
| D453,560 S | 2/2002 | Van Brunt |
| 6,379,316 B1 | 4/2002 | Van Brunt et al. |
| 6,390,790 B1 | 5/2002 | Robertson et al. |
| 6,415,791 B1 | 7/2002 | Van Brunt |
| 6,468,237 B1 | 10/2002 | Lina |
| 6,488,641 B2 | 12/2002 | Hansen |
| 6,526,970 B2 | 3/2003 | DeVries et al. |
| 6,543,449 B1 | 4/2003 | Woodring et al. |
| 6,544,202 B2 | 4/2003 | McEwen et al. |
| 6,558,338 B1 | 5/2003 | Wasserman |
| 6,622,724 B1 | 9/2003 | Truitt et al. |
| 6,666,209 B2 | 12/2003 | Bennett et al. |
| 6,694,978 B1 | 2/2004 | Bennarsten |
| 6,702,769 B1 | 3/2004 | Fowler-Hawkins |
| 6,877,511 B2 | 4/2005 | DeVries et al. |
| D504,945 S | 5/2005 | Van Brunt et al. |
| 6,899,100 B2 | 5/2005 | Wickham et al. |
| 6,910,479 B1 * | 6/2005 | Van Brunt ........... A61H 9/0078 128/200.24 |
| 6,929,007 B2 | 8/2005 | Emerson |
| 6,932,084 B2 | 8/2005 | Estes et al. |
| 6,958,046 B2 | 10/2005 | Warwick et al. |
| 6,984,214 B2 | 1/2006 | Fowler-Hawkins |
| 7,044,129 B1 | 5/2006 | Truschel et al. |
| 7,096,866 B2 | 8/2006 | Be'eri et al. |
| 7,115,104 B2 | 10/2006 | Van Brunt et al. |
| 7,121,808 B2 | 10/2006 | Van Brunt et al. |
| 7,225,809 B1 | 6/2007 | Bowen et al. |
| 7,425,203 B2 | 9/2008 | Van Brunt et al. |
| 7,448,383 B2 | 11/2008 | Delache et al. |
| 7,491,182 B2 | 2/2009 | Van Brunt |
| RE40,814 E | 6/2009 | Van Brunt et al. |
| 7,582,065 B2 | 9/2009 | Van Brunt et al. |
| 7,615,017 B2 | 11/2009 | Van Brunt et al. |
| 7,836,881 B2 | 11/2010 | Lurie et al. |
| 8,025,054 B2 | 9/2011 | Dunsmore et al. |
| 8,038,633 B2 | 10/2011 | Van Brunt et al. |
| 8,066,004 B2 | 11/2011 | Morris et al. |
| 8,074,647 B2 | 12/2011 | Truitt et al. |
| 8,539,852 B2 | 9/2013 | Yamamura |
| 8,539,952 B2 | 9/2013 | Carbone et al. |
| 8,708,937 B2 | 4/2014 | Van Brunt et al. |
| 8,985,112 B2 | 3/2015 | Ikei et al. |
| 2001/0027791 A1 | 10/2001 | Wallace et al. |
| 2002/0016560 A1 | 2/2002 | Hansen |
| 2005/0039749 A1 | 2/2005 | Emerson |
| 2005/0051174 A1 | 3/2005 | Emerson |
| 2005/0172965 A1 | 8/2005 | Thulin |
| 2006/0130835 A1 | 6/2006 | Truschel et al. |
| 2007/0004992 A1 | 1/2007 | Van Brunt et al. |
| 2007/0017522 A1 | 1/2007 | Be-Eri et al. |
| 2007/0186928 A1 | 8/2007 | Be'eri |
| 2008/0000477 A1 * | 1/2008 | Huster ................ A61B 34/25 128/204.23 |
| 2008/0202528 A1 | 8/2008 | Carter et al. |
| 2008/0264419 A1 | 10/2008 | Lomask et al. |
| 2008/0283060 A1 | 11/2008 | Bassin |
| 2009/0126734 A1 | 5/2009 | Dunsmore et al. |
| 2010/0016770 A1 | 1/2010 | Van Brunt et al. |
| 2010/0180897 A1 | 7/2010 | Malgouyres |
| 2011/0220107 A1 | 9/2011 | Kimm et al. |
| 2012/0016282 A1 | 1/2012 | Van Brunt et al. |
| 2014/0150791 A1 * | 6/2014 | Birnkrant ........... A61M 16/024 128/204.23 |
| 2015/0174350 A1 * | 6/2015 | Ikei ..................... A61M 16/20 128/204.21 |
| 2016/0001033 A1 * | 1/2016 | Van De Ven ..... A61M 16/0006 128/205.24 |

FOREIGN PATENT DOCUMENTS

| | | |
|---|---|---|
| EP | 1 897 597 A2 | 3/2008 |
| SE | 143 165 | 12/1953 |
| WO | WO 01/24698 A1 | 4/2001 |
| WO | WO 02/06673 A1 | 1/2002 |
| WO | WO 02/058619 A2 | 8/2002 |
| WO | WO 03/002176 A2 | 1/2003 |
| WO | WO 03/005886 A2 | 1/2003 |
| WO | WO 2006/004439 A2 | 1/2006 |
| WO | WO 2007/055829 A2 | 5/2007 |
| WO | WO 2010/000439 A1 | 1/2010 |

OTHER PUBLICATIONS

Respironics, Cough Assist User Guide, Apr. 24, 2008 (26 pages).
Tatkov, Stanislav et al., "Symmetrical-Waveform High-Frequency Oscillation Increases Artificial Mucus Flow Without Changing Basal Mucus Transport in In Vitro Ovine Trachea," 435 Respiratory Care, vol. 56, No. 4 (Apr. 2011) (7 pages).
Great Ormond Street Hospital for Children NHS Trust, The RC Cornet Information for Families, 2010 (4 pages).
International Search Report and Written Opinion for PCT/US2012/036876, dated Nov. 26, 2012 (8 pages).
Supplementary European Search Report, dated Jul. 29, 2014, in related case, EP 12786272 (9 pages).

* cited by examiner

COORDINATED CONTROL OF HFCWO AND COUGH ASSIST DEVICES

The present application claims the benefit, under 35 U.S.C. § 119(e), of U.S. Provisional Application No. 62/199,714, which was filed Jul. 31, 2015, and which is hereby incorporated by reference herein in its entirety.

BACKGROUND

The present disclosure relates generally to respiratory therapy systems. More specifically, the present disclosure is directed to a respiratory therapy system that includes a high frequency chest wall oscillation (HFCWO) therapy and a Mechanical Insufflation/Exsufflation (MIE) therapy.

Respiratory therapy systems are used to treat a variety of diseases, such as cystic fibrosis, emphysema, asthma and chronic bronchitis, to remove excess mucus that collects in the lungs. Some of the therapies include manual percussion techniques of chest physiotherapy and mechanical insufflation/exsufflation techniques. To bypass dependency on a caregiver to provide respiratory therapy, HFCWO devices and MIE devices have been developed. The HFCWO devices have been developed to deliver HFCWO therapy to a patient's torso to promote airway mucus clearance by generating rapidly oscillating externally powered cough like air flows and pressures in the airways of a patient. The MIE devices have been developed to deliver MIE therapy to a patient by artificially stimulating cough internally to clear airway secretions.

The device most widely used to produce HFCWO therapy is THE VEST™ airway clearance system available from Hill-Rom Company, Inc. An example of such a system is shown and described in U.S. Pat. No. 7,115,104, which is assigned to Hill-Rom Services Pte. Ltd., and which is hereby incorporated by reference herein. Further, an example of an MIE airway clearance apparatus is shown and described in U.S. Pat. No. 8,539,952, which is also assigned to Hill-Rom Services Pte. Ltd., and which is hereby incorporated by reference herein.

SUMMARY

The present application discloses one or more of the features recited in the appended claims and/or the following features which, alone or in any combination, may comprise patentable subject matter:

According to the present disclosure, a respiratory therapy apparatus may include a housing, a high frequency chest wall oscillator (HFCWO) supported in the housing and operationally coupled to a garment worn on a torso of a patient to deliver a HFCWO therapy to the patient. The HFCWO therapy may include application to the garment of a first baseline positive pressure and pressure oscillations relative to the first baseline positive pressure. The respiratory therapy apparatus also may include a mechanical insufflator/exsufflator (MIE) supported in the housing and coupled to the patient's airway via a patient interface to deliver MIE therapy to the patient. The MIE therapy may include cycles of a positive insufflation pressure and a negative exsufflation pressure applied to the patient's airway via the patient interface. The respiratory therapy apparatus may further have a controller situated in the housing and operable to control the HFCWO therapy and the MIE therapy. During application of the negative exsufflation pressure to the patient's airway, the controller may signal the HFCWO to apply a second baseline positive pressure to the garment thereby to provide an extra squeeze to the patient's torso during application of the negative exsufflation pressure to the patient's airway.

In some embodiments, the MIE therapy may further have a rest cycle between each application of negative exsufflation pressure to the patient's airway and the subsequent application of positive insufflation pressure to the patient's airway. During the rest cycle of the MIE, the HFCWO may be controlled by the controller to apply the first baseline pressure and pressure oscillations to the garment. During MIE therapy, the controller may control the MIE to provide oscillations to the positive insufflation pressure or the negative exsufflation pressure or both. In some embodiments, during the rest cycle, the controller may operate the MIE to apply a positive rest pressure to the patient's airway that is less than the positive insufflation pressure.

The controller may have a manual mode in which a user may provide manual input as to when the MIE switches between application of the positive insufflation pressure and the negative exsufflation pressure. The controller may be configured to receive parameter settings for the MIE from a user. The parameter settings may include, for example, the positive insufflation pressure, the negative exsufflation pressure, a rest pressure, and a flutter frequency. Alternatively or additionally, the parameter settings may include an insufflation time, an exsufflation time, a rest time, and a predetermined number of respiratory cycles. The controller may be configured to receive parameter settings from a user for the HFCWO and such the parameter settings may include an oscillation frequency, the first baseline pressure, and the second baseline pressure.

According to the present disclosure, a respiratory therapy apparatus may include a housing, a first therapy delivery apparatus situated in the housing and operable to provide a first respiratory therapy to a patient, a second therapy delivery apparatus situated in the housing and operable to provide a second respiratory therapy to the patient, and a controller operable to control the first therapy delivery apparatus and the second therapy delivery apparatus to deliver a respiratory therapy to the patient. During the respiratory therapy, a positive pressure squeeze may be provided to the patient's torso as part of the first respiratory therapy while a negative pressure is applied to the patient's airway as part of the second respiratory therapy.

In some embodiments, the first respiratory therapy may be a high frequency chest wall oscillation (HFCWO) therapy. Thus, the first therapy delivery apparatus may comprise a high frequency chest wall oscillator operationally coupled to a garment worn by the patient to deliver the HFCWO therapy to the patient. In some embodiments, the second respiratory therapy may be a Mechanical Insufflation-Exsufflation (MIE) therapy. Thus, the second respiratory therapy delivery apparatus may comprise a mechanical insufflator/exsufflator operationally coupled to a patient mask, mouthpiece, or tracheal tube to deliver the MIE therapy to the patient.

In some embodiments, the MIE therapy may include an insufflation mode, an exsufflation mode, and an optional rest mode. During the insufflation mode, the controller may provide the second respiratory therapy to the patient while maintaining the first respiratory therapy at a baseline. During the exsufflation mode, the controller may control the first respiratory therapy apparatus to apply the positive pressure squeeze to the patient's torso. In some embodiments, during the rest mode, the controller may provide the first respiratory therapy to the patient.

It is contemplated by this disclosure that the controller may be configured to accept manual inputs from a user to switch the second respiratory therapy apparatus between an insufflation mode, an exsufflation mode, and a rest mode. Alternatively or additionally, the controller may be configured to receive parameter settings from a user. The parameter settings may include an insufflation time, an exsufflation time, a rest time, and a predetermined number of cycles. Alternatively or additionally, the parameter settings may include an oscillation frequency and a baseline pressure. Further alternatively or additionally, the parameter settings may include an insufflation pressure, an exsufflation pressure, a rest pressure, and a flutter frequency.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

The term "air" as used in the specification and claims is used broadly to include regular or ambient air, medical air, nitrogen, oxygen, and any other breathable, as well as non-breathable, gas available in any location including a hospital or healthcare facility.

A respiratory therapy apparatus 10 includes components operable to provide a first respiratory therapy and a second respiratory therapy to a patient. A controller 80 of the respiratory therapy apparatus 10 coordinates a synchronization of the first respiratory therapy and the second respiratory therapy to effectively clear mucous or induce deep sputum from the lungs of patient.

Figure 1:
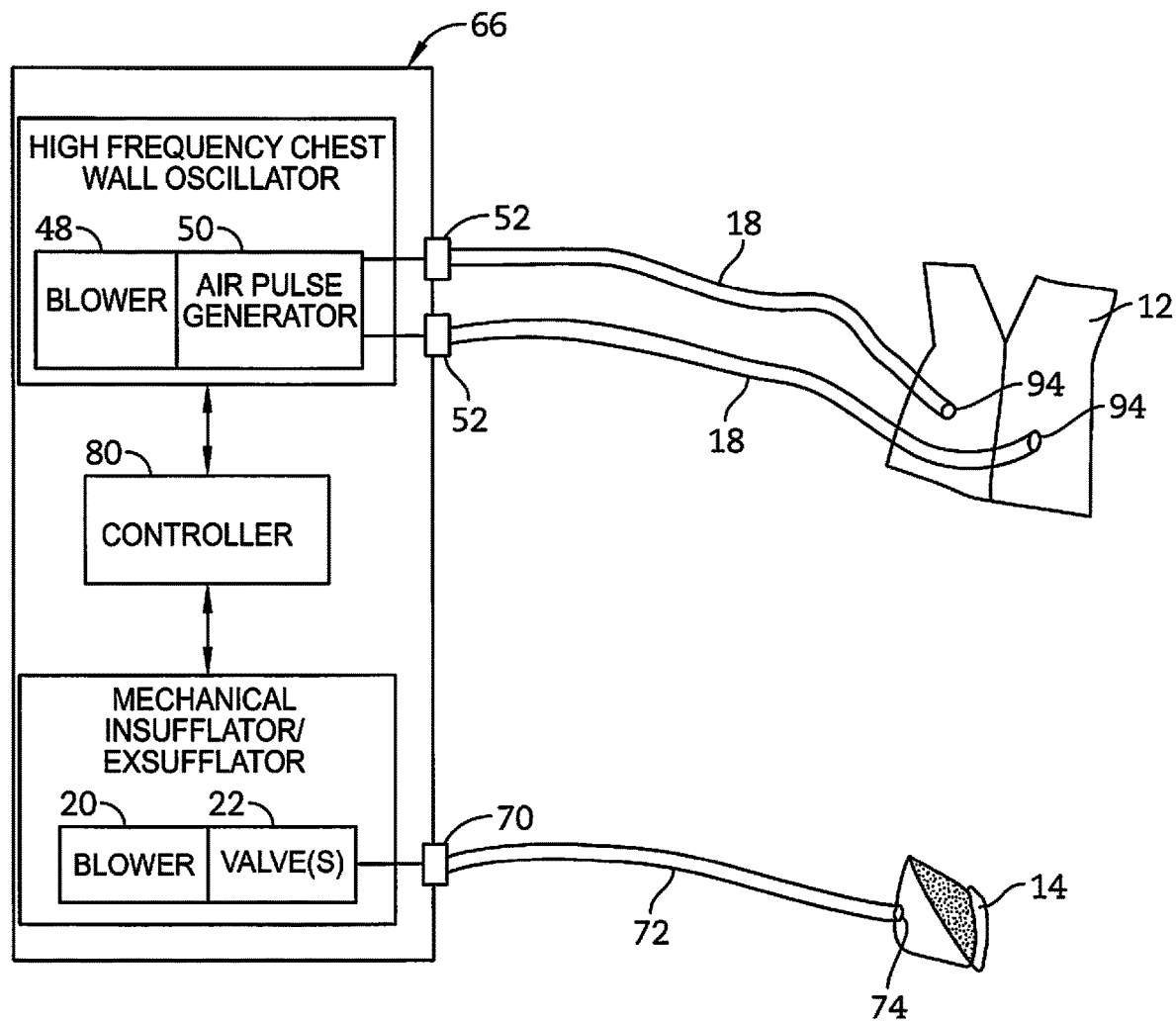
FIG. 1 is a diagrammatic view of a respiratory therapy apparatus including a high frequency chest wall oscillator (HFCWO) and a Mechanical Insufflator/Exsufflator (MIE) connected to a patient vest and a patient mask, respectively, and further including a controller that controls the operation of the HFCWO and MIE simultaneously.

One example of the respiratory therapy apparatus 10 contemplated by the present disclosure is shown diagrammatically in FIG. 1. In the illustrative embodiment, the first respiratory therapy of the respiratory therapy apparatus 10 comprises a High Frequency Chest Wall Oscillation (HFCWO) therapy and the second respiratory therapy of the synchronized respiratory therapy apparatus 10 comprises a Mechanical Insufflation/Exsufflation (MIE) therapy. As shown in FIG. 1, the respiratory therapy apparatus 10 includes a housing 66 that contains a high frequency chest wall oscillator 46, a mechanical insufflator/exsufflator 24, and a controller 80. The high frequency chest wall oscillator 46 generates the HFCWO therapy and the mechanical insufflator/exsufflator 24 generates the MIE therapy. The controller 80 of the respiratory therapy apparatus 10 coordinates the synchronization of the high frequency chest wall oscillator 46 and the mechanical insufflator/exsufflator 24.

The HFCWO therapy components of the respiratory therapy apparatus 10 include the high frequency chest wall oscillator 46, a pair of hose connector ports 52, a pair of hoses 18, and a patient vest 12. Other garments, such as a chest wrap, are used in lieu of vest 12 in some embodiments. Furthermore, embodiments in which only hose 18 is used to communicate the HFCWO therapy to the garment, such as vest 12, are also within the scope of the present disclosure. The high frequency chest wall oscillator 46 further includes a blower 48 and an air pulse generator 50. The patient vest 12 includes an inflatable bladder (not shown) having a pair of air ports 94. The pair of hoses 18 is releasably coupled to the ports 52 of the housing 66 and the ports 94 of the bladder of the patient vest 12. Air pulses from the air pulse generator 50 are routed from the housing 66 of the synchronized respiratory therapy apparatus 10 to the patient vest 12 via the hoses 18.

Figure 3:
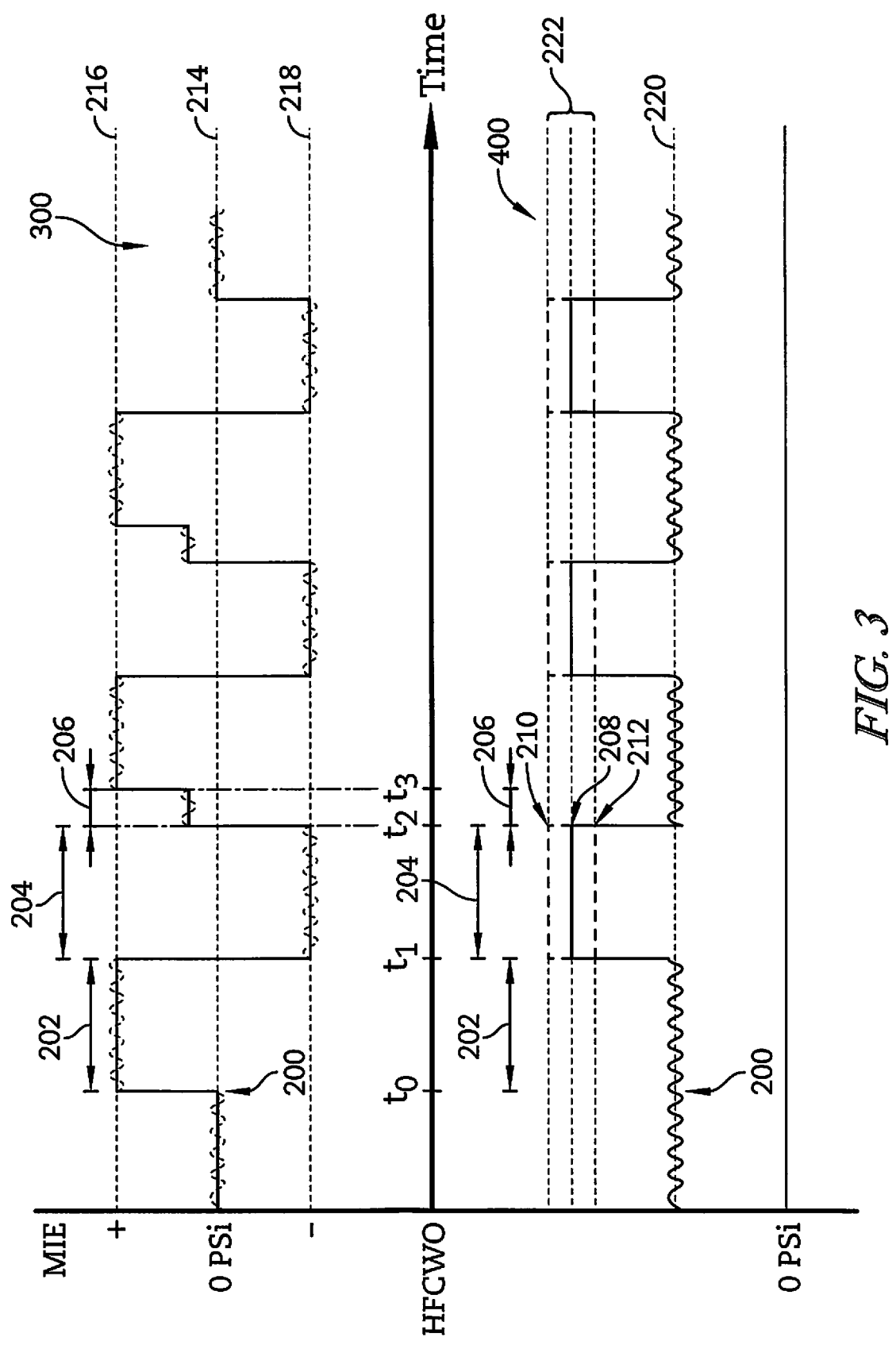
FIG. 3 is a graph that shows a synchronization of a MIE therapy and a HFCWO therapy during operation of the MIE and HFCWO.

In operation, the high frequency chest wall oscillator 46 produces the HFCWO air pulses. Specifically, as shown in FIG. 3, the blower 48 of the high frequency chest wall oscillator 46 produces a pressure having a steady state or baseline air pressure component 220 (sometimes referred to as a "bias line pressure") and the air pulse generator 50 of the high frequency chest wall oscillator 46 produces an oscillating air pressure component 222. The pressure is a resulting composite waveform of the oscillating air pressure component 222 and the steady state air pressure component 220. The oscillating air pressure component 222 is substantially comprised of air pulses, while the steady state air pressure component 220 is substantially comprised of bias line pressure. Therefore, the high frequency chest wall oscillator 46 provides air pulses and a bias pressure to the patient vest 12 positioned on the patient. The air pulses oscillate the patient vest 12, while the bias pressure keeps the patient vest 12 inflated.

The patient vest 12 applies an oscillating compressive force to the chest of the patient. In the illustrative embodiment, the user can manually predetermine the oscillating compressive force and the oscillation frequency. The oscillating compressive force can be manually set to a level ranging from 0 to 10 with a default level of 3. Each level of the oscillating compressive force corresponds to a predetermined pressure of the air pulses which is applied to the chest of the patient. The oscillation frequency can be manually set depending on the mode of the high frequency chest wall oscillator 46. The oscillation frequency is selected depending on the different mode of the high frequency chest wall oscillator 46.

In the some embodiments, the high frequency chest wall oscillator 46 has several different modes including SWEEP, STEP, and MANUAL modes. MANUAL mode allows the high frequency chest wall oscillator 46 to be manually programmed to set the oscillation frequency and bias line pressure. SWEEP mode presets the high frequency chest wall oscillator 46 to sweep over a range of oscillation frequencies while maintaining the same bias or steady state air pressure component 220. SWEEP mode provides three different sweep ranges, although any number or range of frequencies is programmable through user interface (not shown). The three different sweep ranges, which are: HIGH, which sweeps the oscillation frequency between 10 to 20

Hz; NORMAL, which sweeps the oscillation frequency between 7 and 17 Hz; and LOW, which sweeps the oscillation frequency between 5 and 15 Hz. In each of these modes, the oscillation frequency sweeps between the two end points to incrementally change the oscillation frequency. The oscillation frequency incrementally increases until it reaches the high frequency, then incrementally decreases the oscillation frequency to the low frequency, then the cycle is repeated. The oscillation frequency may be configured to incrementally increase to the high frequency, returns to the low frequency, and incrementally increase to the high frequency without incrementally decreasing. The incremental increasing and decreasing continues throughout the treatment, or until the settings are reset. It is believed that the low frequencies are more effective at clearing small airways, and high frequencies more effective at clearing larger airways.

The STEP mode presets the high frequency chest wall oscillator 46 to step over a range of oscillation frequencies while maintaining the same bias or steady state air pressure component 220. The STEP mode provides three different step ranges, although any number or range of frequencies is programmable through user interface (not shown). In each of these modes the oscillation frequencies step from the low frequency to the high frequency, changing the oscillation frequency a fixed amount after a fixed period of time. The oscillation frequency increases by steps until it reaches the high frequency, then decreases the oscillation frequency until the low frequency is reached. Further details of the high frequency chest wall oscillator 46 can be found in U.S. Pat. No. 7,115,104 which is already incorporated by reference herein.

As described above, in the illustrative embodiment, the second respiratory therapy of the respiratory therapy apparatus 10 is the MIE therapy. The MIE therapy includes two primary modes: an insufflation mode 202 and an exsufflation mode 204, that is, inhale and exhale relative to the patient as shown in FIG. 3. To induce a cough, the respiratory therapy apparatus 10 starts in the insufflation mode 202 to fill the lungs. The respiratory therapy apparatus 10 then rapidly transitions to the exsufflation mode 204, rapidly deflating the lungs and thereby stimulating a cough. In addition, the MIE therapy includes an optional rest mode 206 where a positive pressure is set but neither insufflation nor exsufflation is active. The rest pressure is typically a positive pressure that is lower than the positive insufflation pressure.

As shown in FIG. 1, the MIE therapy components include the mechanical insufflator/exsufflator 24, and a hose connector port 70, a hose 72 and a patient mask 14. In some embodiments, a patient interface other than the mask 14, such as a mouthpiece or tracheal tube, is used. The mechanical insufflator/exsufflator 24 further includes a blower 20 and at least one valve 22. In some embodiments, a first valve 22 is used to switch between first and second positions to dictate whether an intake or an exhaust of the blower 20 is coupled to port 70 and therefore, to mask 14 and a second valve 22 that serves as an oscillator between the first valve 22 and the hose connector port 70. In other embodiments, an oscillator other than the second valve 22 is used. When the oscillator operates, this is sometimes referred to as a "flutter" mode which superimposes oscillations on the positive insufflation pressure, the negative exsufflation pressure, and the rest mode as shown (in phantom) in FIG. 3.

As alluded to above, the blower 20 includes a blower intake (not shown) and a blower exhaust (not shown) of the type that are well known in the art. The patient mask 14 includes an air port 74. The hose 72 is releasably coupled to the port 70 of the housing 66 and the port 74 of the patient mask 14. Thus, the air flow is routed from the respiratory therapy apparatus 10 to the patient mask 14 via the hose 72. The blower 20 used in the illustrative configuration is a standard motorized blower with an adjustable speed. It has an intake for suction and an exhaust for blowing. The speed of the blower 20 is controlled by varying the voltage at a control input. In operation, the oscillator is either inactive or is in the "flutter" mode. If the oscillator is inactive, it allows a maximize airflow from the blower 20 to the patient mask 14. If the oscillator is in flutter mode, the air flow rapidly changes from a maximum flow rate to minimal flow rate and back.

In addition, the setting of the valve 22 determines the direction of airflow to the connector port 74 and, ultimately, the patient mask 14. In insufflation mode, the valve 22 connects the blower exhaust to the oscillator, causing a positive flow at the connector port 74, and connects the blower intake to atmosphere as a source of air for the bower 20. In exsufflation mode, the valve 22 connects the blower intake to the oscillator, causing a negative flow at the connector port 74, and connects the blower exhaust to atmosphere for pressure relief. Further details of the mechanical insufflator/exsufflator 24 can be found in U.S. Pat. No. 8,539,952 which is already incorporated by reference herein.

The respiratory therapy apparatus 10 can operate in a manual mode or an automatic mode. In the manual mode, the user controls when and how a treatment cycle occurs by pressing the associated buttons on the touch screen (not shown) or on the remote control (not shown). In the manual mode, several parameters for the mechanical insufflator/exsufflator 24 and the high frequency chest wall oscillator 46 must be set prior to operation. The parameters for the high frequency chest wall oscillator 46 include the oscillation frequency and the bias line pressure. The oscillation frequency is set to a value ranging from 5 Hz to 25 Hz with a default frequency of 12 Hz. The parameters for the mechanical insufflator/exsufflator 24 include an insufflation pressure, an exsufflation pressure, an insufflation time, an exsufflation time, a rest time, a total number of treatment cycles, and a flutter during insufflation/exsufflation.

The insufflation pressure is a positive pressure of the air being pushed into the lungs and can be set in the range of 0-50 cm $H_2O$ in 1 cm $H_2O$ increments. The exsufflation pressure is a negative pressure of the air being pulled from the lungs and can be set in the range of 0-50 cm $H_2O$ in 1 cm $H_2O$ increments. The insufflation time is a length of time that the positive insufflation pressure is active and can be set in the range of 0-3 sec in 0.2 sec increments. The exsufflation time is a length of time that the negative exsufflation pressure is active and can be set in the range of 0-3 sec in 0.2 sec increments. The rest time is a length of time between exsufflation of one cycle and insufflation of the next cycle and can be set in the range of 0-3 sec in 0.2 sec increments. The total number of cycles can be set in the range of 1-99. The user can enable the flutter to assist in the dislodging of mucus in the pulmonary airways.

In the flutter mode, the air flow rapidly changes from maximum flow rate to minimum flow rate. The user can set the flutter rate in the range of 0-20 Hz in 1 Hz increments. The flutter is disabled when the flutter frequency is zero. After the parameters are set, the user touches a start button (not shown) on the synchronized respiratory therapy apparatus 10 to start the synchronized respiratory therapy.

In the automatic mode, the respiratory therapy apparatus 10 repeatedly initiates respiratory treatment cycles. One respiratory treatment cycle includes insufflation, exsufflation, and optional rest periods. Similar to the manual mode, several parameters for the mechanical insufflator/exsufflator 24 and the high frequency chest wall oscillator 46 must be set prior to operation in the automatic mode. The parameters for the high frequency chest wall oscillator 46 include the oscillating compressive force, the oscillation frequency, and the bias line pressure. Likewise, the parameters for the mechanical insufflator/exsufflator 24 include the insufflation pressure, the exsufflation pressure, the insufflation time, the exsufflation time, the rest time, the flow rate, the flutter during insufflation/exsufflation, and the number of treatment cycles. The modified settings are stored in memory of the synchronized respiratory therapy apparatus 10. In some embodiments, the controller 80 determines the last saved setting in the memory and executes that setting during the automatic mode.

Figure 2:
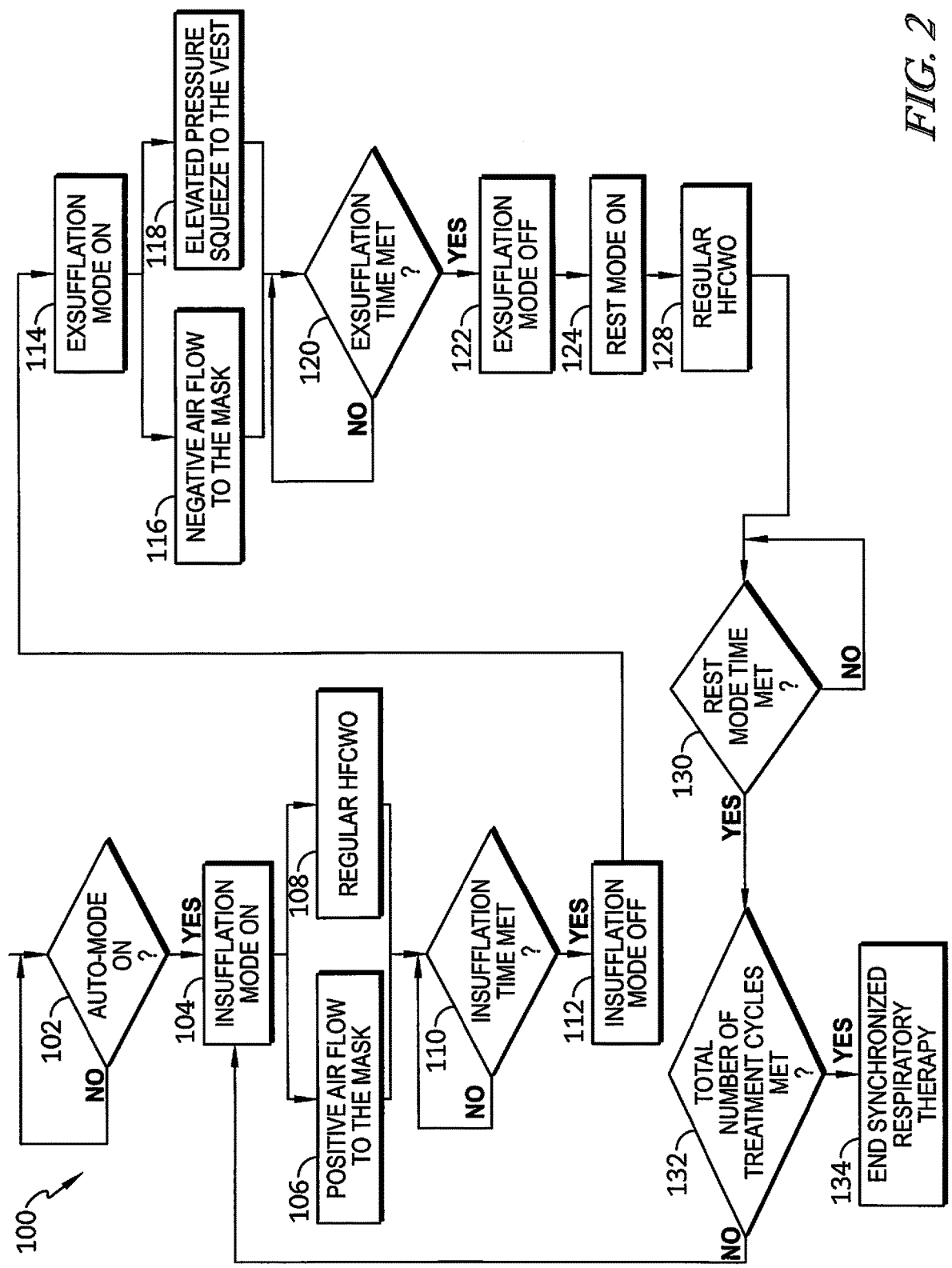
FIG. 2 is a flow chart showing the manner in which the controller controls the respiratory therapy apparatus in an automatic mode in which the MIE operates according to an insufflation period, an exsufflation period, and a rest period and the HFCWO operates regularly during the insufflation and rest periods and applies an elevated pressure squeeze to the patient vest during the exsufflation period.

Referring to FIG. 2, an automatic mode process 100 for providing a synchronized respiratory therapy during one insufflation/exsufflation cycle is shown. The automatic mode process 100 illustratively begins at decision step 102 where the controller 80 is operable to check if the respiratory therapy apparatus 10 is in its automatic mode. If the controller 80 determines that the respiratory therapy apparatus 10 is in automatic mode, the automatic mode process 100 proceeds to step 104 where the controller 80 turns on the insufflation mode 202.

During the insufflation mode 202, the mechanical insufflator/exsufflator 24 applies the positive pressure of air through the patient mask 14 into the patient's lungs while the high frequency chest wall oscillator 46 maintains its regular HFCWO therapy in whatever mode it is programmed to operate. In FIG. 3, the regular HFCWO therapy is illustrated as maintaining a set predetermined steady state air pressure component 220 with oscillations cycling above and below the steady state air pressure component 220. The automatic mode process 100 remains in the insufflation mode 202 until the controller 80 determines that the predetermined insufflation time is reached as indicated at step 110. Once the controller 80 determines that the insufflation time is reached, the automatic mode process 100 proceeds to step 112 where the controller 80 turns the insufflation mode 202 off. The automatic mode process 100, subsequent to turning off the insufflation mode 202, proceeds to step 114 where the controller 80 turns on the exsufflation mode 204.

During the exsufflation mode 204, the mechanical insufflator/exsufflator 24 pulls the negative pressure of the air from the patient's lungs through the patient mask 14 as indicated at block 116. In addition, the high frequency chest wall oscillator 46 provides the predetermined elevated pressure squeeze to the vest 14 as indicated at block 118. Thus, during the exsufflation mode 204, the mechanical insufflator/exsufflator 24 and the high frequency chest wall oscillator 46 operate simultaneously to squeeze the patient's chest or torso and apply negative pressure to the patient's lungs during the exsufflation to clear out the patient's lungs effectively.

The automatic mode process 100 remains in the exsufflation mode 204 until the controller 80 determines that the predetermined exsufflation time is reached as indicated at step 120. Once the controller 80 determines that the exsufflation time is reached, the automatic mode process 100 proceeds to step 122 where the controller 80 turns off the exsufflation mode 204. The automatic mode process 100, subsequent to turning off the exsufflation mode 204, proceeds to step 124 where the controller 80 turns on the rest mode 206.

During the rest mode 206, the positive rest pressure is set but neither insufflation nor exsufflation is active during the rest time. Further, the air pulse generator 50 returns the HFCWO therapy to its regular operation, illustratively, the application of the predetermined steady state air pressure component 220 to the vest 14 as indicated at step 128. The rest time is the length of time between exsufflation of one cycle and insufflation of the next cycle. Once the controller 80 determines that the predetermined rest time is reached, as indicated at step 130, the automatic mode process 100 proceeds to step 132 where the controller 80 further determines whether the total number of treatment cycles is met. If the controller 80 determines that the total number of treatment cycles has not been met, the automatic mode process 100 proceeds back to step 104 where the controller 80 turns the insufflation mode 202 on and starts another cycle. On the contrary, if the controller 80 determines that the total number of treatment cycles is met, the respiratory therapy apparatus 10 discontinues the synchronized respiratory therapy and turns off the mechanical insufflator/exsufflator 24 and the high frequency chest wall oscillator 46.

The automatic mode process 100 is represented in a graphical view in FIG. 3. FIG. 3 includes two pressure traces 300, 400. The top trace 300 represents the pressure applied by the MIE device 24 to the patient mask 14 throughout the synchronized respiratory therapy. The bottom trace 400 represents the pressure applied by the HFCWO device 46 to the patient vest 12 throughout the synchronized respiratory therapy. The automatic mode of the MIE is turned on at 200 and the synchronized respiratory therapy starts at $t_0$ in the insufflation mode 202. As described above, the synchronized respiratory therapy includes three modes: the insufflation mode 202, the exsufflation mode 204, and the rest mode 206.

During the insufflation mode 202, the mechanical insufflator/exsufflator 24 produces the positive pressure to push air into the patient's lungs, whereas the high frequency chest wall oscillator 46 maintains the predetermined steady state air pressure component 220 with oscillations superimposed thereon. The insufflation time ends at $t_1$ and the exsufflation mode 204 starts. During the exsufflation mode 204, the mechanical insufflator/exsufflator 24 and the high frequency chest wall oscillator 46 operate simultaneously to squeeze the patient's lungs as shown in FIG. 3 between $t_1$ and $t_2$. The mechanical insufflator/exsufflator 24 produces the negative pressure to pull the air from the patient's lungs and the high frequency chest wall oscillator 46 is operated to apply the elevated pressure squeeze to the patient's chest. In the illustrative example, no oscillations are produced during the elevated pressure squeeze. In other embodiments, oscillations continue during the elevated pressure squeeze.

As described previously, the baseline pressure of the air pulses can be manually set to a level ranging from 0 to 10. The default level is 3 which is graphically represented by line 220 in FIG. 3. The user can also set the elevated pressure squeeze level which, in the illustrative example, is represented by line segment 208 in FIG. 3 and which corresponds to level 7. Of course, at the option of the user, the elevated pressure can be set to a higher level, for example, level 8 which is represented by dashed line 210 in FIG. 3, or the elevated pressure can be set to a lower level, for example, level 6 which is represented by dashed line 212 in FIG. 3. In some embodiments such as the illustrative embodiment, the elevated pressure is applied to the patient via vest 14 throughout the duration of the exsufflation cycle of the MIE therapy. Thus, the vest 14 applies an extra "squeeze" to the chest or torso of the patient while the negative exsufflation pressure is being applied to the patient's airway. This coordinated action of apparatus 10 produces a more productive cough in the patient than either of the MIE and HFCWO devices 24, 46 are able to produce when acting alone. In other embodiments, the duration of the elevated pressure squeeze of the HFCWO device 46 is less than or greater than the duration of the exsufflation applied by the MIE device 24. The duration time of the elevated pressure squeeze and its phase or positioning relative to the exsufflation cycle is programmable by the user in some embodiments.

The exsufflation time ends at $t_2$ and the rest mode 206 starts. During the rest mode 206, the mechanical insufflator/exsufflator 24 operates at the positive rest pressure. Similarly, the high frequency chest wall oscillator 46 returns to the predetermined steady state air pressure component 220. When the rest time ends at $t_3$, the synchronized respiratory therapy apparatus 10 may continue with another therapy cycle if the total number of preset treatment cycles is not met. Alternatively, the user may manually stop the synchronized respiratory therapy by pressing the stop button (not shown) on the synchronized respiratory therapy apparatus 10.

It should be appreciated that the elevated pressure squeeze disclosed herein occurs during exsufflation when the MIE device 24 is being operated in the manual mode as well as in the automatic mode. Furthermore, the elevated pressure squeeze occurs during exsufflation regardless of which mode (e.g., STEP, SWEEP, MANUAL) the HFCWO device 46 is operating.

Although certain illustrative embodiments and graphical illustrations have been described in detail above, variations and modifications exist within the scope and spirit of this disclosure as described and as defined in the following claims.

The invention claimed is:

1. A respiratory therapy apparatus comprising
a housing;
a high frequency chest wall oscillator (HFCWO) supported in the housing and operationally coupled to a garment worn on a torso of a patient to deliver a HFCWO therapy to the patient, the HFCWO therapy comprising application to the garment of a first baseline positive pressure and pressure oscillations relative to the first baseline positive pressure;
a mechanical insufflator/exsufflator (MIE) supported in the housing and coupled to the patient's airway via a patient interface to deliver MIE therapy to the patient, the MIE therapy comprising cycles of a positive insufflation pressure and a negative exsufflation pressure applied to the patient's airway via the patient interface; and
a controller situated in the housing and operable to control the HFCWO therapy and the MIE therapy, wherein during application of the negative exsufflation pressure to the patient's airway, the controller signals the HFCWO to apply a second baseline positive pressure to the garment thereby to provide an extra squeeze to the patient's torso during application of the negative exsufflation pressure to the patient's airway, wherein the pressure oscillations of the HFCWO therapy are turned off by the controller during the extra squeeze.

2. The respiratory therapy apparatus of claim 1, wherein the MIE therapy further comprises a rest cycle between each application of negative exsufflation pressure to the patient's airway and the subsequent application of positive insufflation pressure to the patient's airway.

3. The respiratory therapy apparatus of claim 2, wherein, during the rest cycle of the MIE, the HFCWO is controlled by the controller to apply the first baseline pressure and pressure oscillations to the garment.

4. The respiratory therapy apparatus of claim 2, wherein during MIE therapy, the controller controls the MIE to provide oscillations to the positive insufflation pressure or the negative exsufflation pressure or both.

5. The respiratory therapy apparatus of claim 2, wherein, during the rest cycle, the controller operates the MIE to apply a positive rest pressure to the patient's airway that is less than the positive insufflation pressure.

6. The respiratory therapy apparatus of claim 2, wherein the controller has a manual mode in which a user provides manual input as to when the MIE switches between application of the positive insufflation pressure and the negative exsufflation pressure.

7. The respiratory therapy apparatus of claim 2, wherein the controller is configured to receive parameter settings for the MIE from a user, the parameter settings including the positive insufflation pressure, the negative exsufflation pressure, a rest pressure, and a flutter frequency.

8. The respiratory therapy apparatus of claim 1, wherein the controller is configured to receive parameter settings from a user for the MIE, the parameter settings including an insufflation time, an exsufflation time, a rest time, and a predetermined number of respiratory cycles.

9. The respiratory therapy apparatus of claim 1, wherein the controller is configured to receive parameter settings from a user for the HFCWO, the parameter settings including an oscillation frequency, the first baseline pressure, and the second baseline pressure.

10. A respiratory therapy apparatus comprising
a housing;
a first therapy delivery apparatus situated in the housing and operable to provide a first respiratory therapy to a patient;
a second therapy delivery apparatus situated in the housing and operable to provide a second respiratory therapy to the patient; and
a controller operable to control the first therapy delivery apparatus and the second therapy delivery apparatus to deliver a respiratory therapy to the patient, wherein during the first and second respiratory therapy, an oscillatory positive pressure having a first baseline pressure is provided to the patient's torso as part of the first respiratory therapy while a positive pressure is applied to the patient's airway as part of the second respiratory therapy and a nonoscillatory positive pressure squeeze at a second baseline pressure is provided to the patient's torso as part of the first respiratory therapy while a negative pressure is applied to the patient's airway as part of the second respiratory therapy, the second baseline pressure being greater than the first baseline pressure.

11. The respiratory therapy apparatus of claim 10, wherein the first respiratory therapy is a high frequency chest wall oscillation (HFCWO) therapy.

12. The respiratory therapy apparatus of claim 11, wherein the first therapy delivery apparatus comprises a high frequency chest wall oscillator operationally coupled to a garment worn by the patient to deliver the HFCWO therapy to the patient.

13. The respiratory therapy apparatus of claim 10, wherein the second respiratory therapy comprises a Mechanical Insufflation-Exsufflation (MIE) therapy.

14. The respiratory therapy apparatus of claim 13, wherein the second respiratory therapy delivery apparatus comprises a mechanical insufflator/exsufflator operationally coupled to a patient mask, mouthpiece, or tracheal tube to deliver the MIE therapy to the patient.

15. The respiratory therapy apparatus of claim 13, wherein the MIE therapy includes an insufflation mode, an exsufflation mode, and an optional rest mode.

16. The respiratory therapy apparatus of claim 15, wherein, during the insufflation mode, the controller provides the second respiratory therapy to the patient while maintaining the first respiratory therapy at a baseline.

17. The respiratory therapy apparatus of claim 15, wherein, during the exsufflation mode, the controller controls the first respiratory therapy apparatus to apply the positive pressure squeeze to the patient's torso.

18. The respiratory therapy apparatus of claim 15, wherein, during the rest mode, the controller provides the first respiratory therapy to the patient.

19. The respiratory therapy apparatus of claim 10, wherein the controller is configured to accept manual inputs from a user to switch the second respiratory therapy apparatus between an insufflation mode, an exsufflation mode, and a rest mode.

20. The respiratory therapy apparatus of claim 10, wherein the controller is configured to receive parameter settings from a user, the parameter settings including an insufflation time, an exsufflation time, a rest time, and a predetermined number of cycles.

21. The respiratory therapy apparatus of claim 10, wherein the controller is configured to receive parameter settings from a user, the parameter settings including an oscillation frequency and a baseline pressure.

22. The respiratory therapy apparatus of claim 10, wherein the controller is configured to receive parameter settings from a user, the parameter settings including an insufflation pressure, an exsufflation pressure, a rest pressure, and a flutter frequency.

\* \* \* \* \*